Figure 1:
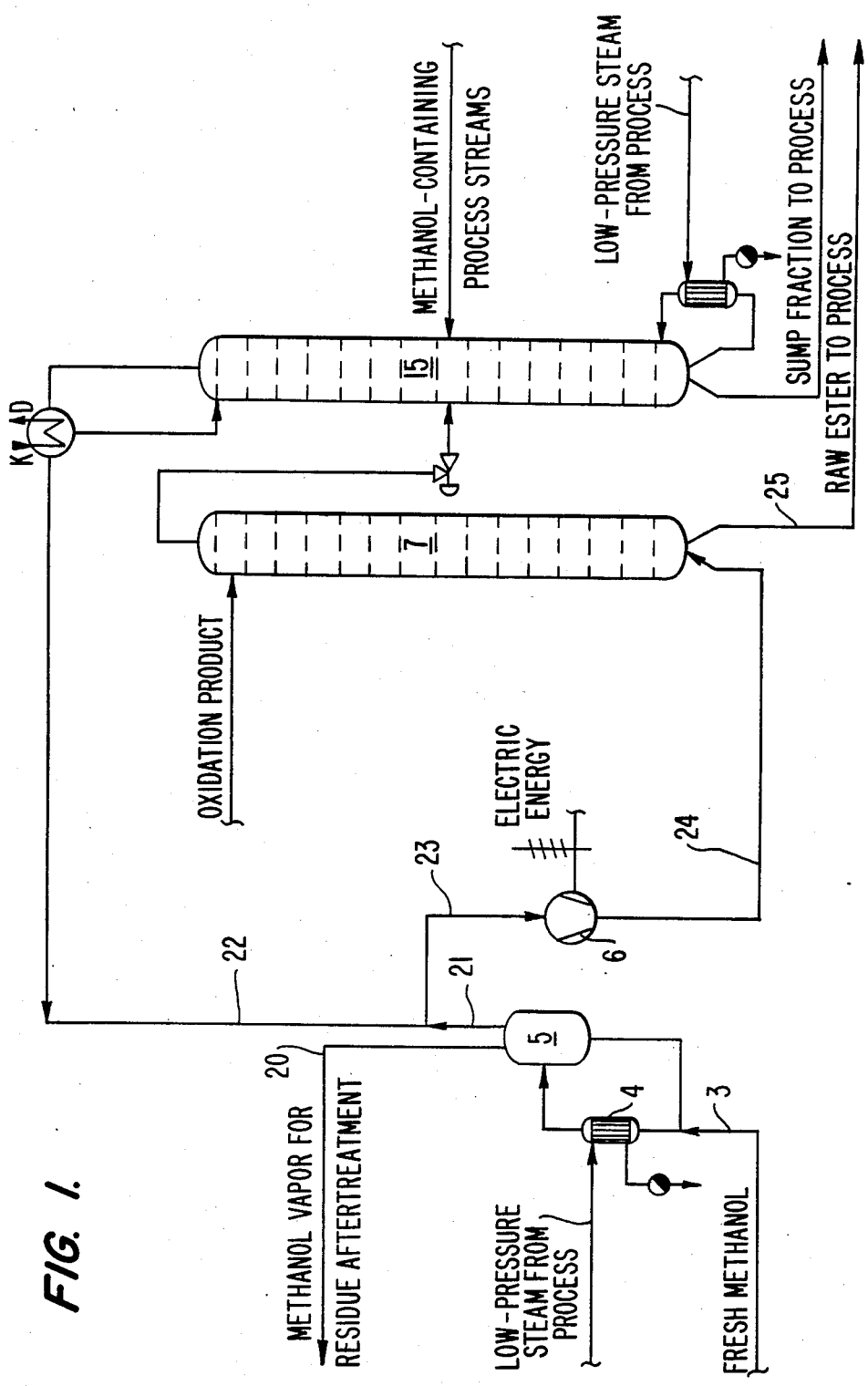

United States Patent [19]

Modic et al.

[11] Patent Number: 4,642,377

[45] Date of Patent: Feb. 10, 1987

[54] PROCESS FOR PRODUCING TEREPHTHALIC ACID FROM P-XYLENE AND METHANOL BY WAY OF DIMETHYL TEREPHTHALATE

[75] Inventors: Rudolf Modic, Steyerberg; Jörg Porschen, Düren; Anton Schoengen, Witten; Ralf Wirges, Niederkassel, all of Fed. Rep. of Germany

[73] Assignee: Dynamit Nobel Aktiengesellschaft, Troisdorf, Fed. Rep. of Germany

[21] Appl. No.: 707,579

[22] Filed: Mar. 4, 1985

[30] Foreign Application Priority Data

Mar. 3, 1984 [DE] Fed. Rep. of Germany ....... 3407912

[51] Int. Cl.⁴ ............................................. C07C 51/09
[52] U.S. Cl. ................................... 562/483; 562/412; 562/413; 562/414
[58] Field of Search ................ 562/412, 413, 414, 483

[56] References Cited

U.S. PATENT DOCUMENTS 2,653,165  9/1953  Levine ........................... 562/483 X
4,302,595 11/1981  Schoengen et al. ................ 562/483

Primary Examiner—Natalie Trousof
Assistant Examiner—Vera C. Clarke
Attorney, Agent, or Firm—Antonelli, Terry & Wands

[57] ABSTRACT

A process for the production of terephthalic acid from p-xylene and methanol by way of the dimethyl terephthalate obtained by oxidation, in the liquid phase with atmospheric oxygen in the presence of dissolved heavy metal compounds as the catalyst, of a mixture of p-xylene and a fraction containing predominantly methyl p-toluate, which fraction is recycled into the oxidation, to obtain an oxidation product containing primarily p-toluic acid and monomethyl terephthalate at a temperature of 140°–170° C. and under a pressure of 4–8 bar; by esterification of the oxidation product in a reactor with liquid and subsequently vaporized methanol brought to an elevated pressure, at a temperature of 220°–280° C. and under a pressure of 20–25 bar to obtain a raw ester containing primarily methyl p-toluate and dimethyl terephthalate; by withdrawing the raw ester fraction and a methanol-containing vapor fraction from the esterification reactor; by distillatory separation of the raw ester into a methyl p-toluate fraction and a fraction rich in terephthalic aldehyde methyl ester, which fractions are recycled into the oxidation, a raw dimethyl terephthalate fraction, and a residual fraction; and by hydrolysis of the raw dimethyl terephthalate fraction with water, obtaining the thus-formed terephthalic acid and separation of a methanol-water mixture. In this process, the methanol-containing vapor fraction and the methanol-water mixture are separated by rectification under elevated pressure and elevated temperature into a methanol-rich head fraction and an aqueous sump phase, the methanol formed at the head of the rectification stage is withdrawn in vapor phase under elevated pressure, and esterification of the oxidation product is conducted with the methanol-containing vapor brought by compression to esterification pressure and esterification temperature.

9 Claims, 1 Drawing Figure

PROCESS FOR PRODUCING TEREPHTHALIC ACID FROM P-XYLENE AND METHANOL BY WAY OF DIMETHYL TEREPHTHALATE

The invention relates to a process for the production of terephthalic acid (TPA) from p-xylene (p-X) and methanol, via the formation of dimethyl terephthalate (DMT) by the Witten-DMT process as disclosed, for example, in German Pat. No. 1,041,945 and U.S. Pat. No. 2,894,978.

More particularly, this invention is directed to a process for the production of terephthalic acid (TPA) from p-xylene (p-X) and methanol by way of dimethyl terephthalate (DMT) by oxidation, in the liquid phase with atmospheric oxygen in the presence of heavy metal catalyst, of a mixture of p-X and a fraction containing predominantly methyl p-toluate (p-TE) in a reactor, the fraction being recycled into the oxidation, to obtain an oxidation product containing primarily p-toluic acid (p-TA) and monomethyl terephthalate (MMT), at an elevated temperature and under an elevated pressure; by esterification of the oxidation product with liquid and subsequently vaporized methanol brought to an elevated pressure, at an elevated temperature and under an elevated pressure in a reactor to obtain a raw ester product containing primarily p-TE and DMT; by withdrawing a fraction containing the raw ester product and a fraction containing methanol vapor from the esterification reactor; by distillatory separation of the raw ester product into a p-TE fraction and a fraction rich in terephthalic aldehyde methyl ester, which fractions are recycled into the oxidation reactor, a raw DMT fraction, and a residual fraction; and by hydrolysis of the raw DMT fraction with water thereby obtaining TPA, and separation of a methanol-water mixture; wherein the methanol used as a reactant in the esterification reactor is obtained by treatment of methanol-containing process streams in a compressor and the thus-compressed methanol is compressed to the pressure and heated to the temperature required for esterification. The production of TPA by the hydrolysis of an intermediate stage crude DMT obtained by the Witten-DMT process is also disclosed in U S. Pat. No. 4,302,595.

In a known process (cf. "Hydrocarbon Processing" Nov., 1983, pp. 91 and 151), the oxidized product of the oxidation is esterified with methanol to a raw ester product in an esterification reactor. The weight ratio of methanol to oxidized product is approximately between 0.2:1 and 1.0:1. Only about 30–50% of the amount of methanol charged into the esterification reactor in the large-scale industrial procedure is required for the esterification reaction. The remainder of methanol serves to shift the esterification equilibrium in the direction of a maximally complete esterification of the oxidized product and, furthermore, to provide an energy-transfer medium, and a transport medium for the water produced during the esterification reaction. The methanol vapor used in the esterification is introduced into the esterification in a superheated state at a temperature of about 0–50° C. above the esterification temperature.

The hydrolysis reaction is performed, for example, in a multistage single reactor by introducing, at the head, a raw DMT having a temperature of 350–140° C. and, at the bottom of the hydrolysis reactor, steam having a temperature of 180–350° C., and, with a conversion rate of above 90%, an aqueous phase which contains terephthalic acid is withdrawn from the bottom and a methanol-water mixture is removed from the head of the reactor (see DOS 3,044,617).

In a mode of operation, heretofore practiced, a methanol-water mixture was recovered from the methanol-containing aqueous mother liquor obtained in the hydrolysis reaction, by means of distillation. The vapors produced during rectification of the mixture were condensed and pumped into a storage tank for the reaction methanol; i.e., the methanol to be introduced into the esterification reactor. The methanol was taken from the tank for reaction methanol, brought by way of high-pressure pumps to, for example, a pressure of 27 bar, heated under this pressure, and vaporized, then superheated, for example, to about 250–270° C., and fed into the esterification reactor.

The disadvantage of this mode of operation resides in that the methanol used for effecting esterification is twice vaporized.

Considerable economical interest has existed in improving the reaction methanol supply that would lead to a more advantageous process, from an energy viewpoint, for the production of terephthalic acid in large-scale industrial plants than the conventional system operating with a two-fold methanol vaporization.

This object has been attained by the process of the present invention.

The proposed procedure of supplying the esterification stage with reaction methanol at the required pressure and temperature level is conducted so that reaction methanol is obtained, under a pressure lying below the esterification pressure, by rectification of the methanol-containing vapor fraction from the esterification reactor and other methanol-containing process streams, as well as of the methanol-containing process stream from the hydrolysis; and that the methanol vapors are subsequently compressed to the pressure utilized during esterification, the heat of compression being exploited for increasing the temperature of the methanol vapor to the temperature required during esterification. The methanol-containing vapor utilized for esterification is also produced by utilizing fresh methanol serving to compensate for methanol losses, by vaporization as well as by rectification of the methanol-containing vapor fraction from the esterification and of other methanol-containing process streams, as well as of the methanol-containing process stream from the hydrolysis, under a pressure of 2–20 bar, preferably 4–8 bar. The utilized fresh methanol is vaporized suitably under the same pressure as prevailing during rectification of the methanol-containing vapor fraction from the esterification and other methanol-containing process streams as well as of the methanol-containing process stream from the hydrolysis. The fresh methanol to be used can, however, also be fed directly into the rectification of the methanol-containing vapor fraction from the esterification and other methanol-containing process streams, as well as of the methanol-containing process stream from the hydrolysis. The compression ratio of the methanol-containing vapor subjected to compression is generally adjusted to a value of between 1.2:1 and 15:1, preferably 3:1 and 9:1; the final temperatures of the reaction methanol leaving the compressor, attained during compression, are at a temperature of between 150° and 300° C., preferably 220–280° C.

The energy of the vapors made up of excess methanol and reaction water, discharged from the esterification reactor; namely, from the head of the esterification reactor, can advantageously be utilized, after washing with process water or also with dephlegmated reflux from the esterification reactor, by expansion in a turbine.

The primary effect in the proposed novel process resides in that valuable primary energy can be saved, in the form of high-pressure steam (17–25 bar) or heat-transfer media.

The process of this invention will be described hereinafter in greater detail with reference to a FIGURE of the accompanying drawings, wherein:

The sole FIGURE is a schematic diagram of the apparatus for conducting the process of this invention.

The methanol required to cover processing losses is fed as fresh methanol into conduit 3. In the forced circulation evaporator 4, the methanol is vaporized by way of the vaporizing vessel 5 under a pressure of about 4–8 bar. The forced circulation evaporator is heated with low-pressure steam obtained at another location in the process. Part of the methanol can be supplied via conduit 20 to a residue aftertreatment stage for the reactive aftertreatment of residual fractions from the distillatory processing of the raw ester. The methanol intended for esterification is withdrawn via conduit 21 in vapor phase from the head of the vaporizer vessel 5. In a rectifying column 15, the esterification vapors, containing methanol and reaction water, are fractionated together with the remaining methanol-containing process streams into an aqueous sump fraction and a methanol-containing head fraction. This head fraction is fed via conduits 22 and 23 to the compressor 6 together with the methanol vapor obtained at the vaporizer vessel 5 and compressed to about 25–30 bar, where simultaneously superheating occurs to about 220–280° C., and the resulting methanol finally is fed to the esterification reactor 7 via conduit 24. The oxidation product is introduced into the head of the esterification reactor 7.

The raw ester product is withdrawn from the sump of the esterification reactor 7 via conduit 25, and the methanol-containing vapors are obtained at the head of reactor 7.

What is claimed is:

1. A process for the production of terephthalic acid from p-xylene and methanol by way of dimethyl terephthalate obtained by oxidation, in the liquid phase with atmospheric oxygen in the presence of dissolved heavy metal compounds as the catalyst, of a mixture of p-xylene and a fraction containing predominantly methyl p-toluate, which fraction is recycled into the oxidation, to obtain an oxidation product containing primarily p-toluic acid and monomethyl terephthalate at a temperature of 140–170° C. and under a pressure of 4–8 bar; by esterification of the oxidation product in a reactor with liquid and subsequently vaporized methanol brought to an elevated pressure, at a temperature of 220–280° C. and under a pressure of 20–25 bar to obtain a raw ester containing primarily methyl p-toluate and dimethyl terephthalate; by withdrawing the raw ester fraction and a methanol-containing vapor fraction from the esterification reactor; by distillatory separation of the raw ester into a methyl p-toluate fraction and a fraction rich in terephthalic aldehyde methyl ester, which fractions are recycled into the oxidation, a raw dimethyl terephthalate fraction, and a residual fraction; by hydrolysis of the raw dimethyl terephthalate fraction with water, obtaining the thus-formed terephthalic acid and separation of a methanol-water mixture, characterized in that the methanol-containing vapor fraction and the methanol-water mixture are separated by rectification under elevated pressure and elevated temperature into a methanol-rich head fraction and an aqueous sump phase, the methanol formed at the head of the rectification stage is withdrawn in vapor phase under elevated pressure, and esterification of the oxidation product is conducted with the methanol-containing vapor brought by compression to esterification pressure and esterification temperature.

2. A process according to claim 1, characterized in that the methanol-containing vapor utilized for esterification is produced by rectification under a pressure of 2–20 bar.

3. A process according to claim 1, characterized in that the methanol-containing vapor utilized for esterification is produced by rectification under a pressure of 4–8 bar.

4. A process according to claim 1, characterized in that the heat produced during compression of the methanol-containing vapor serves for superheating the methanol-containing vapor to the esterification temperature.

5. A process according to claim 1, characterized in that the compression ratio of the methanol-containing vapor subjected to compression is 1.2:1 to 15:1, and the final temperature at the compressor outlet, attained during compression, is 150–300° C.

6. A process according to claim 1, characterized in that the compression ratio of the methanol-containing vapor subjected to compression is 3:1 to 9:1, and the final temperature at the compressor outlet, attained during compression, is 220–280° C.

7. A process according to claim 1, characterized in that the vapors withdrawn from the esterification reactor are washed and subsequently expanded in a vapor expansion turbine to 0.1 to 8 bar for driving the methanol compressor and are subsequently recycled into the process.

8. A process according to claim 7, characterized in that the vapors are partially condensed prior to entering the compressor and a portion of the condensate is utilized for the vapor washing step.

9. A process according to claim 7, characterized in that the vapors are washed with process water.

* * * * *